(12) United States Patent
Raut

(10) Patent No.: US 7,084,157 B2
(45) Date of Patent: Aug. 1, 2006

(54) OPHTHALMIC PHARMACEUTICAL COMPOSITIONS AND METHODS FOR TREATING OCULAR INFLAMMATION

(76) Inventor: Rajeev Raut, 46 Hermes Heritage, Pune 6 (IN)

( * ) Notice: Subject to any disclaimer, the term of this patent is extended or adjusted under 35 U.S.C. 154(b) by 393 days.

(21) Appl. No.: 10/209,837

(22) Filed: Aug. 1, 2002

(65) Prior Publication Data

US 2003/0216431 A1 Nov. 20, 2003

Related U.S. Application Data

(60) Provisional application No. 60/380,926, filed on May 17, 2002.

(51) Int. Cl.
*A61K 31/47* (2006.01)
*A61K 31/60* (2006.01)
*A61K 31/535* (2006.01)
*A61K 31/501* (2006.01)

(52) U.S. Cl. .................. 514/313; 514/165; 514/235.2; 514/252.04; 514/314; 514/921

(58) Field of Classification Search ............... 514/313, 514/165, 235.2, 252.04, 256, 314
See application file for complete search history.

(56) References Cited

U.S. PATENT DOCUMENTS 5,596,002 A * 1/1997 Hofheinz et al. ........... 514/313
5,948,791 A * 9/1999 Hofheinz et al. ........... 514/313

OTHER PUBLICATIONS

Windholz et al., The Merck Index, 1983, Tenth Edition, pp. 304-305, abstract No. 2136; and p. 123, absract No. 863.*
Avunduk, AM, et al., Mechanisms and Comparison of Anti-allergic efficacy of Topical Lodoxamide and Cromolyn Sodium Treatment in Vernal Keratoconjunctivitis (2000), Ophthalmology, vol. 107, No. 7, pp. 1333-1337.
Cordes, OD, et al., Plaquenil Toxicity in a Young Patient: Yes or No? (2002), The Southern Journal of Optometry, www.optcom.com/sjo/cordes.htm, pp. 1-6.
De Campos, AM, et al., Chitosan Nanoparticles: A New Vehicle for the Improvement of the Delivery of Drugs to th Ocular Surface. Application to Cyclosporin A (2001), Int. J Pharm, vol. 224, No. 1-2, pp. 159-168.
Dellaert, MMMJ, et al, Influence of Topical Human Epidermal Growth Factor on Postkeratoplasty Re-Epitheliali (May 1997), Br. J. Ophthalmol., vol. 81, pp. 391-395.
Gonzalez Alonso-Alegre, EM, et al., Comparison of Cyclosporin A and Dexamethasone in the Treatment of Canine Nictitans Plasmacytic Conjunctivitis (Jun. 19, 1999) The Veterinary Record, vol. 144, No. 25, pp. 696-701.
Grant, WM, vol. I, Toxicology of the Eye, 2d Ed., pp. 272-273.
Guidera, AC, et al., Keratitis, Ulceration, and Perforation Associated with Topical Nonsteroidal Anti-Inflammatory Drugs (May 2001), Ophthalmology, vol. 108, No. 5, pp. 936-944.
Hillenkamp, J, et al., The Effects of Cidofovir 1% with and without Cyclosporin A 1% as a Topical Treatment of Acute Adenoviral Keratoconjunctivitis, a Controlled Clinical Pilot Study (May 2002), Ophthalmology, vol. 109, No. 5, pp. 845-850.
Kulkarni, P, Review: Uveitis and Immunosuppressive Drugs (2001), Journal of Ocular Pharmacology and Therapeutics, vol. 17, No. 2, pp. 181-187.
Jones, Ocular Toxicity and Hydroxychloroquine; Guidelines for Screening (1999), British Journal of Dermatology, vol. 140, No. 1, pp. 3-7.
Olsen, EG, et al., The Effect of Steroids on the Healing of the Corneal Endothelium, an In Vivo and In Vitro Study in Rabbits (1984), ACTA Ophthalmologica, vol. 62, No. 6, pp. 893-899.
Rynes, RI, Antimalarial Drugs in the Treatment of Rheumatological Diseases (1997), British Journal of Rheumatology, vol. 36, No. 7, pp. 799-805.
Van Der Bijl, P, Effects of Three Penetration Enhancers on Transcorneal Permeation of Cyclosporine (2001), Cornea, No. 20, vol. 5, pp. 505-508.

* cited by examiner

Primary Examiner—Kevin E. Weddington
(74) Attorney, Agent, or Firm—Nancy Lord

(57) ABSTRACT

The present invention relates to novel ophthalmic pharmaceutical compositions comprising an inflammation-treating amount of a 4-aminoquinoline compound, derivative, isomers, or chemical salts, and methods for using these compositions for the treatment of ocular inflammatory conditions by topical administration directly to the eye.

1 Claim, No Drawings

OPHTHALMIC PHARMACEUTICAL COMPOSITIONS AND METHODS FOR TREATING OCULAR INFLAMMATION

This application claims the benefit of U.S. Provisional Application No. 60/380,926 filed May 17, 2002.

FIELD OF THE INVENTION

This invention relates to the treatment of ocular inflammation of varied etiology such as immune disease factors, surgery, chemical or mechanical injury, injury due to exposure to radiation, infrared or ultraviolet rays, degenerative changes or dystrophies, allergic or infective etiology.

More particularly, this invention relates to ophthalmic pharmaceutical compositions comprising a 4-aminoquinoline compounds, used for the treatment of malaria and rheumatoid arthritis, and methods for treating ocular inflammation with said compositions. This invention relates to a method of administration of 4-aminoquinolines as ophthalmic pharmaceutical compositions that permits administration of 4-aminoquinolines directly to the eye, through corneal, conjunctival, subconjunctival and intravitreal routes for attaining sustained ocular levels of the active agent, without oral or parenteral administration. Ocular administration avoids the severe side effects of systemically administered 4-aminoquinolines while attaining effective dosage levels in the eye. Chloroquine, a representative generic drug, has never been used to treat the eye by the composition and method described herein.

BACKGROUND OF THE INVENTION

Inflammatory disorders of the eye have historically been recognized as complex and vision threatening. Although numerous pharmaceutical agents and compositions exist for its treatment, their side effects profile and effectiveness are less than desired. The side effects may not be acceptable in a particular patient, or if prolonged use is required. The current invention provides a new and original method for treatment of ocular inflammation.

Inflammation of the eye may be localized to the eye, the eyes, or may be part of more generalized inflammatory process. Its etiology may be infection, allergy, immunological reactions, or as a response to surgery, injury, or due to any other causes. The ocular inflammation causes pain, irritation, watering, threatens visual function of the eye and may also change optical properties of the eye. Inflammation may be seen as uveitis or keratoconjunctivitis.

Uveitis is an inflammation of the uvea, the middle layer of tissue behind the white of the eye. The cause of uveitis is poorly understood, but a variety of systemic diseases are associated with it. Uveitis has been treated by various classes of compounds including steroids and nonsteroidal anti-inflammatory agents such as dexamethasone, flurometholone, prednisolone, indomethacin, aspirin, flubiprofen and diclofenac. However, a number of uveitic cases are not responsive to or become refractory to these drugs. Kulkarni, P., 17(2) JOURNAL OF OCULAR PHARMACOLOGY AND THERAPEUTICS 181–7 (2001). Serious side effects including cataract, glaucoma, delayed wound healing, and altered prostaglandin production, Id., at 181, and corneal complications including ulceration, perforation, and corneal and scleral melts have been reported with the use of topical nonsteroidal anti-inflammatory drugs. Guidera, A C, Luchs, J I, Udell, I J, 108 OPHTHALMOLOGY 936–944 (2001). Steroids are known to cause increased ocular pressure, cataracts, superinfections, and reduced immunity to infection. Olsen, E G & Davanger M, 62(6) ACTA OPHTALMOL 893–9 (1984).

A newer immunosuppressive, Tacrolimus, is used orally in uveitis, but may cause severe side effects similar to those seen with cyclosporin including renal dysfunction, and neurological disorders. Kulkarni, at 183. The use of Cyclosporin A is further limited by its low penetration into the eye. Van der Bijl, P, van Eyk, A D & Meyer, D 20(5) CORNEA 505–8, 505 (2001). Aldose reductase inhibitors have also been used, especially in diabetics. U.S. Pat. No. 4,600,717, to York. Fibronectin has also been tried to improve healing, but the defect closure rate was unaltered in the treated group. Phan, T M 30(3) Invest Ophthamol Vis Sci 377–385, 381 (1989).

Mast cell stabilizers such as topical Lodoxamide and Cromolyn Sodium have been used to treat vernal keratoconjunctivitis. Avunduk, A M, et al, 107 OPHTHALMOLOGY 1333–1337(2000). Nedrocromil sodium has a safety profile similar to cromolyn sodium. Verin P J, Dicker I D, Mortemousque B, 29(4) CLIN EXP ALLERGY 529–36 (1999). Vernal keratoconjunctivits is often controlled with topical steroids, but the vision threatening side effects are worse than the underlying disease, which usually is self-limiting and resolves as the patient grows up. Verin, 28(S6) ALLERGY 44—(1998)

Immunosuppressives such as topical Cyclosporin A have been used in the treatment of Mooren's ulcer, vernal keratoconjunctivitis, ulcerative keratitis associated with rheumatoid arthritis, anterior uveitis, and Thygeson's punctate keratitis. Kulkarni, P., 109 OPHTHALMOLOGY 845–850 (2002). Recurrence may occur in some patients. Field, A J, Gottsch, J D, 23(4) AUST N ZEALAND J OPHTHALMOLOGY 333–334 (1995). Cidofovir 1% has been used in acute adenoviral keratoconjunctivits but is limited by local toxicity including conjunctival injection chemiosis and punctate epithelial keratitis during the course of treatment and subepithelial infiltrates. It may cause an atypical and uncomfortable erythema of the skin of the eyelids and pronounced conjunctival injection that could be differentiated from adenoviral conjunctival inflammation alone. Hillenkamp, et al 109 OPHTHALMOLOGY 845–850, 847 (2002).

Researchers have studied the use of human epidermal growth factor on postkeratoplasty re-epithelialisation without success, in spite of promising earlier animal data no benefit on epithelial healing. Dellaert M J, et al, 81 BR J OPHTHALMOL 391–395 (1997).

Accordingly, a need exists for novel ophthalmic pharmaceutical compositions which safely and effectively treat ocular inflammation conditions.

It was disclosed that the 4-aminoquinolines have strong anti-inflammatory action and are useful for treatment of inflammatory diseases. Rynes, R I, 36 BR J RHEUMATOL 799–805 (1997). However, there has been no report or study in ophthalmologic field. The anti-inflammatory properties of the anti-malarial 4-aminoquinoline pharmaceuticals are well known. They have not been used to treat inflammation of the eye because their systemic use in high doses has been associated with a rare, but serious, incidence of ocular toxicity including corneal deposits known as verticillata, loss of foveal reflex, impairment of accommodation, maculopathy and retinopathy. These effects may be reversible or irreversible.

Retinopathy is the major and potentially most serious as it is irreversible. Jones, S K, 140(1) BRIT J DERMATOL 3–7, (1999). Ocular toxicity, however, is believed to occur only when doses exceed 6.5 mg/kg/day for a minimum of five (5) years. Cordes, M G, 2000 Southern J Optometry, Poster (2000). The dosage of chloroquine appears to be the most fundamentally important factor in determining the risk of development of retinopathy. In general, it appears that serious retinopathy in nearly all instances is caused by taking more than 250 mg of chloroquine diphosphate or 200 mg of chloroquine sulfate per day to a total amount greater than 100 gms. By not exceeding this daily dosage, it has been found possible for patients to take chloroquine for as long as nine years without developing clinically evident retinopathy. In most cases in which dosage slightly greater than 250 mg chloroquine diphosphate per day has been administered, the onset of definite retinopathy has taken one to three years. According to Nylander, most patients who have developed retinopathy have received nearly a total of 300 gms for three or more years. TOXICOLOGY OF THE EYE, Vol. 1, 272 (Grant, M., ed, $2^{nd}$ Edition).

This inventor has discovered that when used directly in the eye, the 4-aminoquinoline compounds are non-toxic and highly effective in a wide variety of ocular inflammatory disorders. The 4-aminoquinoline compounds used here in novel ophthalmic pharmaceutical compositions have been previously reported to be useful as therapeutics in the treatment of malaria and rheumatoid arthritis. See, for example, U.S. Pat. No. 4,421,920 to Baudouin, U.S. Pat. No. 5,596,002, to Hofheinz, U.S. Pat. No. 5,948,791, also to Hofheinz.

SUMMARY OF THE INVENTION

It has now been found that certain 4-aminoquinoline compounds are useful for preventing and treating ocular inflammation by application of the compositions to the eye prior to, during and after an inflammatory disorder, especially inflammation of the outer and middle coats of the eye, such as dry eye, conjunctivitis, scleritis, keratitis, and uveitis.

The first object of the invention is to provide a novel method by way of route and concentration for the delivery of 4-aminoquinoline drugs directly to the eye for improved effectiveness to treat inflammatory disorders of the eye.

Another object of the invention is to provide prolonged stable intraocular levels of 4-aminoquinolines.

A further object of the invention is to provide sustained intraocular levels of 4-aminoquinolines without having to increase their plasma levels.

Yet another object of the invention is to provide an improved long term administration method for delivering 4-aminoquinolines to patients suffering from inflammatory disorders of the eye.

The objects of the invention are met and the problems and shortcomings associated with systemic administration are overcome by the incorporation of the 4-aminoquinlines into a composition to be administered topically, directly to the eye, as eye drops, eye ointments, gels, a spray via an adsorbent contact lens, via a sustained release container placed in the eye, or subconjunctivally or intravitreally by direct injection. This new treatment technique and delivery method unexpectedly results in a prolonged and sustained intraocular levels of the active drug in mammals using formulations that not necessarily increase drug plasma levels, and therefore avoid hazards associated with raised plasma levels and consequent risk of drug toxicity.

Compounds suitable for delivery using this method include chloroquine, amodiaquine, an isomer or a salt thereof, and structurally similar compounds. As used above, the term "salt thereof" is meant to include any nontoxic pharmaceutically suitable salt of a compound described above with the desired pharmacological properties in mammals. Preparation of such a salt is well-known to those skilled in pharmaceutical science.

DETAILED DESCRIPTION OF THE INVENTION

This inventor has discovered that the 4-aminoquinoline compounds are non-toxic to the eye when administered directly to the eye. Ocular administration permits the compound to be administered in adequate ocular doses and to maintain intraocular levels of the compound for prolonged periods. The 4-aminoquinoline compounds, when used in ophthalmic pharmaceutical compositions, are effective in treating ocular inflammation of varied etiology such as immune disease factors, surgery, chemical or mechanical injury, injury due to exposure to radiation, infrared or ultraviolet rays, degenerative changes or dystrophies; urticaria, allergic conjunctivitis, vernal conjunctivitis, allergic responses in the eye, iritis, iridocyclitis, scleritis, episcleritis, chorioiditis, optic neuritis, Mooren's ulcer, ulcerative keratitis associated with rheumatoid arthritis, anterior uveitis, Thygeson's punctate keratitis, or other immunological reactions; chlamydia, amoeba, adenovirus, cytomegalovirus, toxoplasmosis, tuberculosis, or syphilis; uveitis due to Behect's disease, pars planitis, idiopathic uveitis, ocular sarcoid, sympathetic ophthalmia, idiopathic vitritis, vitritis, or uveitis resulting from trauma.

4-aminoquinolines and their derivatives which are particularly suitable for the method of the present invention and processes for preparing these compositions are disclosed in U.S. Pat. No. 4,421,920 to Baudouin, U.S. Pat. No. 5,596, 002, to Hofheinz, and U.S. Pat. No. 5,948,791, to Hofheinz. To the extent these applications and patents disclose 4-aminoquinoline compounds and their derivatives which are useful in the practice of the present invention, they are incorporated herein by reference.

Detailed descriptions of the preferred embodiment are provided herein; however, it is to be understood that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

As discussed above, the ophthalmic pharmaceutical compositions of this invention contain one or more aminoquinoline compounds as the active component(s). Prior to describing this invention in further detail, the following terms will first be defined.

Definitions

The term "lower-alkyl" used in the present description denotes straight-chain or branched saturated hydrocarbon residues such as methyl, ethyl, n-propyl, isopropyl, n-butyl, isobutyl, s-butyl, t-butyl and the like. "Halogen" is chorine, bromine, fluorine or iodine. When A in formula I is an aliphatic hydrocarbon chain, branched chains, for example —CH(CH$_3$)—CH$_2$—, —CH$_2$CH(CH$_3$)— or —CH$_2$C(CH$_3$)$_2$—, are especially preferred.

The term "cycloalkylene" embraces preferably cyclopentyl or cyclohexyl.

The term "aryl" embraces conveniently phenyl or substituted phenyl, with the number of substituents preferably being 1–3 and the substituents being selected from a group consisting of halogen, hydroxy, lower-alkyl, lower-alkoxy, CF$_3$, cyano, di-lower-alkylamino or their N-oxides, phenyloxy, phenyl or methylsulphanyl.

Furthermore, the term "aryl" conveniently embraces naphthyl, benzo[1,3]dioxol or mono- or bicyclic aromatic heterocycles with 1 or 2 hetero atoms, especially N and/or O, for example pyridyl, quinolyl or furyl. Rings such as phenyl, pyridin-2-yl, pyridin-3-yl, pyridin-4-yl, naphthalen-1-yl, naphthalen-2-yl, furan-2-yl, furan-3-yl or quinolin-4-yl are preferred.

Preferred compounds of general formula I are especially those in which $R^9$ is chlorine, $R^{10}$ is hydrogen, p is 1, A is —$CH_2C(CH_3)_2$— and B is a benzene ring which is unsubstituted, mono-substituted or di-substituted.

"Pharmaceutically acceptable salt" refers to pharmaceutically acceptable salts which are derived from a variety of organic and inorganic counter ions well known in the art and include, by way of example only, sodium, potassium, calcium, magnesium, ammonium, tetraalkyl-ammonium, and the like; and when the molecule contains a basic functionality, salts of organic or inorganic acids, such as hydrochloride, hydrobromide, hydroiodide, tartrate, mesylate, acetate, maleate, bitartarate, lactate, phosphate, malate, maleate, fumarate, succinate, acetate, palmoate, oxalate and the like. Among the conventional salts which can be utilized there are the base salt, for example, alkali metal salts such as sodium or potassium, alkaline earth metal salts such as sodium or potassium, alkaline earth metal salts such as calcium or magnesium, and ammonium or alkyl ammonium salts.

4-Aminoquinoline Compounds

Accordingly, in one of its composition aspects, this invention is directed to an ophthalmic pharmaceutical composition comprising a pharmaceutically acceptable ophthalmic carrier and an ocular inflammation-treating amount of a 4-aminoquinoline compound of formula I:

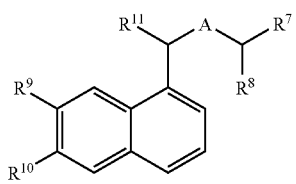

wherein
A is

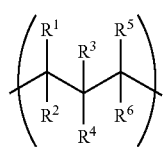

—$(C(R^3)(R^4))_n$—;
and $R^1$ to $R^6$ are hydrogen or in which one or two of $R^1$ to $R^6$ are independently selected from alkyl and the other substituents are hydrogen; $R^7$ and $R^8$ are independently selected from alkyl, alkenyl or aralkyl, or together with the N atom signify pyrrolidine or piperidine, either or both of which may be substituted by alkyl; and n=0 or 1; or wherein $R^1$ and $R^3$ are tri- or tetramethylene; $R^2$ and $R^4$ to $R^6$ are hydrogen; n=0; and $R^7$ and $R^8$ are defined as above; or wherein $R^1$ and $R^7$ are methylene or dimethylene and n=1, or $R^3$ and $R^7$ are di- or trimethylene and n=0, or $R^3$ and $R^7$ are di- or trimethylene and n=1, or $R^3$ and $R^7$ are tri- or tetramethylene and n=0, or $R^5$ and $R^7$ are tri- or tetramethylene and n=1, or $R^1$ and $R^5$ are di- or tri-methylene and n=1, and the remaining substituents are hydrogen, except $R^8$ which is selected from alkyl, alkenyl or alkynyl; or wherein $R^3$ and $R^5$ are tri- or tetramethylene and n=1; $R^1$, $R^2$, $R^4$ and $R^6$ are hydrogen; and $R^7$ and $R^8$ are selected from alkyl, alkenyl or aralkyl or together with the N atom are pyrrolidine or piperidine, either or both of which may be substituted by alkyl;

$R^9$ is hydrogen or halogen; and $R^{10}$ is halogen or trifluoromethyl;

$R^{11}$ is a hydrogen atom or an alkyl radical (1–5 carbon atoms);

In another of its composition aspects, the 4-aminoquinoline compound of Formula 1, A is

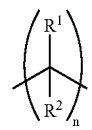

or $(C_5–C_6)$-cycloalkylene; n is 1–4;
or $R^7$ is hydrogen and $R^8$ is $(CH_2)_p$-B and p is 1–3 and B is aryl selected from phenyl, phenyl mono-, di-, or tri-substituted by substituent from the group consisting of halogen, hydroxy, lower alkyl, lower alkoxy, trifluoromethyl, cyano, di-lower alkylamino or their N-oxides, phenyloxy, phenyl, and methylsuphanyl, naphthyl, benzo[1,3]dioxol, or monocyclic aromatic heterocycle with 1 or 2 heteroatoms selected from N and O;

and $R^9$ is hydrogen or halogen; and $R^{10}$ is halogen or trifluoromethyl; as well as pharmaceutically acceptable salts of basic compounds of formula I.

In the third of its composition aspects, the 4-aminoquinoline of Formula I is

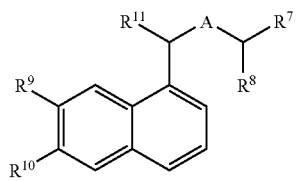

wherein A is an alkyl of 1 through 5 carbon atoms substituted by a dialkylamino group of which each alkyl radical contains 1 through 4 carbon atoms, phenyl, or phenyl substituted by one or more radicals selected from carboxy and hydroxy and alkyl radicals of 1 through 4 carbon atoms and $R^9$ is hydrogen or halogen; and $R^{10}$ is halogen or trifluoromethyl.

Compounds of general formula I in which $R^9$ is hydrogen, $R^{10}$ is chlorine are preferred embodiments:

$N_2$-(7-chloro-quinolin-4-yl)-$N_1$,$N_1$-dimethyl-ethane-1,2-diamine, $N_2$-(7-chloro-quinolin-4-yl)-$N_1$,$N_1$-diethyl-ethane-1,2-diamine, $N_3$-(7-chloro-quinolin-4-yl)-$N_1$,$N_1$-dimethyl-propane-1,3-diamine,
$N_3$-(7-chloro-quinolin-4-yl)-$N_1$,$N_1$-diethyl-propane-1,3-diamine,
(RS)(7-chloro-quinolin-4-yl)-(1-methyl-pyrrolidin-2-yl-methyl)-amine,
(RS)(7-chloro-quinolin-4-yl)-(1-ethyl-piperidin-3-yl)-amine,
(RS)-$N_2$-(7-chloro-quinolin-4-yl)-$N_1$,$N_1$-dimethyl-propane-1,2-diamine,
(RS)-$N_2$-(7-chloro-quinolin-4-yl)-$N_1$,$N_1$-diethyl-propane-1,2-diamine,
(S)-$N_2$-(7-chloro-quinolin-4-yl)-$N_1$,$N_1$-diethyl-propane-1,2-diamine,
(R)-$N_2$-(7-chloro-quinolin-4-yl)-$N_1$,$N_1$-diethyl-propane-1,2-diamine,
(RS)-(7-chloro-quinolin-4-yl)-(1-methyl-2-pyrrolidin-1-yl-ethyl)-amine,
(R)-$N_1$-(7-chloro-quinolin-4-yl)-$N_2$,$N_2$-dimethyl-propane-1,2-diamine,
(S)-$N_1$-(7-chloro-quinolin-4-yl)-$N_2$,$N_2$-dimethyl-propane-1,2-diamine,
or the pharmaceutically acceptable salts of these compounds.

In another preferred embodiment, the ophthalmic pharmaceutical composition 4-aminoquinoline compound in the ophthalmic pharmaceutical composition is selected from the group consisting of:
(S)-$N_2$-(7-chloro-quinolin-4-yl)-$N_1$,$N_1$-dimethyl-propane-1,2-diamine,
(R)-$N_2$-(7-chloro-quinolin-4-yl)-$N_1$,$N_1$-dimethyl-propane-1,2-diamine,
$N_1$-(7-chloro-quinolin-4-yl)-2,$N_2$,$N_2$-trimethyl-propane-1,2-diamine,
(RS)-(7-chloro-quinolin-4-yl)-(1-methyl-pyrrolidin-3-yl)-amine,
or the pharmaceutically acceptable salts of these compounds.

In yet another preferred embodiment, B may be selected from the group consisting of phenyl; naphthyl; benzo[1,3] dioxol and phenyl substituted with from 1–3 substituents selected from the group consisting of halogen, hydroxy, lower-alkyl, lower-alkoxy, trifluoromethyl, cyano, di-lower-alkyl-amino, N-oxides of di-lower-alkyl-amino, phenyloxy, phenyl and methylsulphanyl.

Preferred compounds of general formula I are especially those in which $R^9$ is hydrogen, $R^{10}$ is chlorine, p is 1, A is —$CH_2$—$(CH_3)_2$— and B is a benzene ring which is unsubstituted, mono-substituted or di-substituted.
$N_1$-(7-Chloro-quinolin-4-yl)-$N_2$-(3-chloro-benzyl)-2-methyl-propane-1,2-diamine,
$N_1$-(7-chloro-quinolin-4-yl)-$N_2$-(2-hydroxy-3-methoxy-benzyl)-2-methyl-propane-1,2-diamine,
$N_1$-(7-chloro-quinolin-4-yl)-$N_2$-(2-hydroxy-5-methoxy-benzyl)-2-methyl-propane-1,2-diamine,
$N_1$-(7-chloro-quinolin-4-yl)-$N_2$-(4-hydroxy-3-methoxy-benzyl)-2-methyl-propane-1,2-diamine,
$N_1$-(7-chloro-quinolin-4-yl)-$N_2$(benzyl)-2-methyl-propane-1,2-diamine, Compounds of general formula I in which $R^9$ is hydrogen, $R^{10}$ is chlorine, p is 1, A is cyclohexane-1,2-diyl or cyclohexane-1,4-diyl and B is a benzene ring which is unsubstituted or mono- or di-substituted are also preferred:
(1S,2S)-$N_1$-(7-Chloro-quinolin-4-yl)-$N_2$-(benzyl)-cyclohexane-1,2-diamine,
(1S,2S)-$N_1$-(7-chloro-quinolin-4-yl)-$N_2$-(4-chloro-benzyl)-cyclohexane-1,2-diamine,
(1S,2S)-$N_1$-(7-chloro-quinolin-4-yl)-$N_2$-(4-dimethylamino-benzyl)-cyclo-hexane-1,2-diamine,
cis-$N_1$-(7-chloro-quinolin-4-yl)-$N_4$-(4-dimethylamino-benzyl)-cyclohexane-1,4-diamine,
cis-$N_1$-(7-chloro-quinolin-4-yl)-$N_4$-(benzyl)-cyclohexane-1,4-diamine,
cis-$N_1$-(7-chloro-quinolin-4-yl)-$N_4$-(3-chloro-benzyl)-cyclohexane-1,4-diamine,
cis-$N_1$-(7-chloro-quinolin-4-yl)-$N_4$-(2-hydroxy-4-methoxy-benzyl)-cyclohexane-1,4-diamine,
cis-$N_1$-(7-chloro-quinolin-4-yl)-$N_4$-(3,5-dimethoxy-benzyl)-cyclohexane-1,4-diamine,
cis-$N_1$-(7-chloro-quinolin-4-yl)-$N_4$-(4-methylsulphanyl-benzyl)-cyclohexane-1,4-diamine,
cis-$N_1$-(7-chloro-quinolin-4-yl)-$N_4$-(4-diethylamino-benzyl)-cyclohexane-1,4-diamine,
cis-$N_1$-(7-chloro-quinolin-4-yl)-$N_4$-(biphenyl-4-ylmethyl)-cyclohexane-1,4-diamine,
trans-$N_1$-(7-chloro-quinolin-4-yl)-$N_4$-[2-(3,5-dimethoxy-phenyl)-ethyl]-cyclohexane-1,4-diamine,
cis-$N_1$-(7-chloro-quinolin-4-yl)-$N_4$-(4-methoxy-benzyl)-cyclohexane-1,4-diamine,
trans-$N_1$-(7-chloro-quinolin-4-yl)-$N_4$-(4-dimethylamino-benzyl)-cyclohexane-1,4-diamine and trans-$N_1$-(7-chloro-quinolin-4-yl)-$N_4$-(2,6-difluoro-benzyl)-cyclohexane-1,4-diamine.

Most preferably, the 4-aminoquinoline compound in the ophthalmic pharmaceutical composition is:
Chloroquine phosphate
Quinoline, 7-chloro-4-((4-(diethylamino)-1-methylbutyl)amino)-, sulfate,
Quinoline, 4-((4-(bis(2-chloroethyl)amino)-1-methylbutyl)amino)-7-chloro-, dihydrochloride N,N-Dideethylchloroquine,
Quinoline, 4-(2-(bis(2-chloroethyl)amino)ethylamino)-7-chloro-, dihydrochloride, monohydrate,
Quinoline, 7-chloro-4-((4-(diethylamino)-1-methylbutyl)amino)-, diphosphate, (-)-,
Quinoline, 4-(p-bis(2-chloroethyl)aminophenylethylamino)-7-chloro-, monohydrochloride
Chloroquine
3-Methylchloroquine
Salicylic acid, 4-acetamido-, compd. with 7-chloro-4-((4-(diethylamino)-1-methylbutyl)amino)quinoline,
Hydroxychloroquine
Quinoline, 7-chloro-4-((4-(diethylamino)-1-methylbutyl)amino)-, mixed with sodium nitrite
Hydroxychloroquine sulfate,
Quinoline, 7-chloro-4-((4-(diethylamino)-1-methylbutyl)amino)-, diphosphate,
Quinoline, 7-chloro-4-((4-(diethylamino)-1-methylbutyl)amino)-, phosphate,
Desethylchloroquine.
Chloroquine hydrochloride,
L-Ascorbic acid, compd. with $N(^4)$-(7-chloro-4-quinolinyl)-$N(^1)$,$N(^1)$-diethyl-1,4-pentanediamine,
N,N-Dideethylchloroquine
Amodiaquine In another embodiment, the 4-aminoquinoline compound in the ophthalmic pharmaceutical composition is mefloquine, quinacrine (mepacrine), pyrimethamine, and cletoquine.

General Synthetic Procedures

The 4-aminoquinoline compounds and their derivatives employed in this invention are either commercially available or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protecting and deprotecting various functional groups are well known in the art. For example, numerous protecting groups, and their introduction and removal, are described in T. W. Greene and G. M. Wuts, Protecting Groups in Organic Synthesis, Second Edition, Wiley, New York, 1991, and references cited therein.

In a preferred method of synthesis, the novel compounds of formula I can be manufactured in accordance with the invention by reacting appropriate quinoline derivatives of the general formula with appropriate amino compounds or reacting alkylamino-quinoline derivatives with amines according to the process of Hofheinz, U.S. Pat. No. 5,596,002.

In another preferred method of synthesis, the novel compounds of formula I can be manufactured by a) reducing an appropriate Schiff's base or b) reacting an appropriate amine with a compound of the formula $X$—$(CH_2)_p$-B IV wherein X is a leaving group and the other substituents have the significance described in the process taught by Hofheinz, U.S. Pat. No. 5,948,791.

In yet another preferred method of synthesis the products of the general formula (I) can be obtained, with good yields and virtually free of dechlorinated product, by condensing an appropriate amine with a chloro-1,2,3,4-tetrahydroquinolin-4-one, the reaction being carried out in the presence of a ruthenium based catalyst on a support and preferably in the absence of oxygen, according to the method of Baudouin, U.S. Pat. No. 4,421,920.

The following formulation examples illustrate representative pharmaceutical compositions suitable for ophthalmic delivery of the 4-aminoquinoline compounds used in this invention. The present invention, however, is not limited to the following exemplified pharmaceutical compositions.

Formulation

The ophthalmic pharmaceutical composition of the invention includes one or more additional ophthalmic pharmaceutical compositions including buffers, surfactants, stabilizers, preservatives, ophthalmic wetting agents, ophthalmic diluting agents.

Wetting agents commonly used in ophthalmic solutions include carboxymethylcellulose, hydroxypropyl methylcellulose, glycerin, mannitol, polyvinyl alcohol or hydroxyethylcellulose and the diluting agent may be water, distilled water, sterile water, or artificial tears, wherein the wetting agent is present in an amount of about 0.001% to about 10%.

In another embodiment, the ophthalmic pharmaceutical composition further comprises one or more additional pharmaceutically active ophthalmic pharmaceutical compositions such as anti inflammatory agents, antibiotics, anti fungals, anti virals, ocular hypotensive agents, local anaesthetic agents, cycloplegics, or pupillary dilators used in the treatment of diseases of the eye.

Examples of ophthalmic solutions and ophthalmic ointments can be formulated into such preparations utilizing a number of widely-used methods well known to those of ordinary skill in the art. In the case of ophthalmic solutions, for example, they can be prepared using distilled water, an aqueous base, or any other acceptable base; tonicity agents such as sodium chloride and concentrated glycerol; buffers such as sodium phosphate and sodium acetate; surfactants such as polyoxyethylene sorbitan monooleate, stearic polyoxyl 40, and polyoxyethylene hydrogenated castor oil; stabilizers such as sodium citrate and sodium edetate; preservatives such as benzalkonium chloride, thimerosal, chlorobutanol, sodium chloride, boric acid, parahydroxybenzoic acid esters (sorbate, benzoate, propionate), chlorobutanol, benzyl alcohol, mercurials, paraben; etc., and mixtures thereof, if necessary. Benzalkonium chloride and thimerosal are the preferred preservatives.

The formulation of this invention may be varied to include acids and bases to adjust the pH; tonicity imparting agents such as sorbitol, glycerin and dextrose; other viscosity imparting agents such as sodium carboxymethylcellulose, microcrystalline cellulose, polyvinylpyrrolidone, polyvinyl alcohol and other gums; suitable absorption enhancers, such as surfactants, bile acids; stabilizing agents such as antioxidants, like bisulfites and ascorbates; metal chelating agents, such as sodium edetate; and drug solubility enhancers, such as polyethylene glycols. These additional ingredients help make commercial solutions with adequate stability so that they need not be compounded on demand.

In a preferred embodiment, benzalkonium chloride is added as an antimicrobial preservative in an amount ranging from about 0.001 to about 0.02 weight percent, preferably 0.01 weight percent. In another preferred embodiment, thimerosal is added as an antimicrobial preservative in an amount ranging from about 0.005 to about 0.02 weight percent.

In another embodiment of the invention, the ophthalmic carrier is a surfactant such as a polyoxyethylene fatty acid ester, polyoxyethylene alkylphenyl ether, and polyoxyethylene alkyl ether, or mixtures thereof or a thickening agent such as a carboxyvinyl polymer, polyvinyl polymer, and polyvinylpyrrolidones, as taught by U.S. Pat. No. 5,951,971, to Kawashima.

In the ophthalmic pharmaceutical composition of this invention, the ophthalmic carrier is preferably a sterile aqueous carrier or a salve or ointment carrier. Such salves or ointments typically comprise one or more 4-aminoquinoline compounds dissolved or suspended in a sterile pharmaceutically acceptable salve or ointment base, such as a mineral oil-white petrolatum base. In salve or ointment compositions, anhydrous lanolin may also be included in the formulation. Thimerosal or chlorobutanol are also preferably added to such ointment compositions as antimicrobial agents.

In yet another embodiment of the invention, the ophthalmic carrier may be olive oil, arachis oil, castor oil, polyoxyethylated castor oil, mineral oil, petroleum jelly, dimethyl sulphoxide, an alcohol, liposome, silicone fluid and mixtures thereof as taught by U.S. Pat. No. 6,254,860, to Garst.

Preferably, the active ingredient, namely a 4 aminoquinoline, is found in a concentration between 0.001 nanogram per milliliter to 10 mg per milliliter, in a pharmaceutically acceptable carrier.

The ophthalmic 4-aminoquinoline compositions may be incorporated into liposomes. The use of liposomes as drug delivery systems has been known for some time, and comprehensive review articles on their properties and clinical applications are available; see, e.g., Barenholz and Amselem, in "Liposome Technology", 2nd ed., G. Gregoriadis, ed., CRC press, 1992; Lichtenberg and Barenholz, in Methods for Biochemical Analysis, 33, D. Glick, ed., 1988. A liposome is defined as a structure consisting of one or more concentric lipid bilayers separated by water or aqueous buffer compartments. These hollow structures, which have an internal aqueous compartment, can be prepared with diameters ranging from 20 nm to 10 µm. U.S. Pat. No. 5,576,016, to Amselem. The compositions may be incorporated in nanoemulsions of particles comprising a lipid core composed of lipid which is in a solid or liquid crystalline phase at at least 25° C., stabilized by at least one phospholipid envelope, for the parenteral, oral, rectal, intranasal, or topical delivery of both fat-soluble and water-soluble drugs according to the method of U.S. Pat. No. 5,576,016, to Amselem.

The dose can be appropriately selected depending upon symptom, age, dosage form, etc. and, in the ophthalmic solutions, contain between about 0.001 nanograms per milliliter and 10.00 milligrams per milliliter of a 4-aminoquinoline derivative., preferably between 0.001 nanograms per milliliter and 1.00 milligram per milliliter and most preferably about 0.3 milligrams per milliliter of a 4-aminoquinoline derivative or a salt or isomer of a 4-aminoquinoline derivative in a pharmaceutically acceptable ophthalmic carrier. The pH can be within a range which is acceptable to ophthalmic preparations and, preferably within a range from 4 to 8.

Any of the disclosed 4-aminoquinoline derivatives may be incorporated into chitosan nanoparticles to improve the delivery of the 4-aminoquinoline derivatives to the ocular mucosa, as described by De Campos, Am, Sanchez, A and Alonso M J 224 (1–2) INT J PHARM 159–68, 161 (2001). In one example, the solution is prepared by adding a variable volume of a 4-aminoquinoline compound solution in an acetonitrile/water mixture is incorporated into to Chitosan SeaCure 123, purchased from Pronova Biopolymer AS of Norway (4 mg, 0.2 or 0.5% w/v). Nano particles are formed upon the addition of Sodium tripolyphosphate aqueous solution (0.5 ml, 0.2% w/v) under magnetic stirring at room temperature, purified by centrifugation at 900×g in a glucose bed for 30 minutes. Supernatants are discarded and nanoparticles are resuspended in pure water.

Other materials as well as processing techniques and the like are set forth in Part 8 of Remington's Pharmaceutical Sciences, 17th edition, 1985, Mack Publishing Company, Easton, Pa., and International Programme on Chemical Safety (IPCS), which is incorporated herein by reference.

Mixtures of two or more 4-aminoquinoline compounds may be employed, if desired, in the pharmaceutical compositions and methods of this invention.

EXAMPLES

Representative examples for preparing ophthalmic solutions and ophthalmic ointment of 4-aminoquinoline compounds are shown as follows.

The drops may be combined with other anti inflammatory agents, anti biotics, anti fungals, anti virals, ocular hypotensive agents.

The drops may be combined with artificial tears and ocular lubricants. The drops may be combined with buffers, surface tension lowering agents, local anaesthetic agents, cycloplegics, pupillary dilators, eyedrop formulations used in treatment of eye diseases. The generally used range of pH can be used for this preparation, but a preferable range is 4–8. Depending on the salt of chloroquine used, the pH of the solution may be adjusted by using hydrochloric acid or sodium hydroxide, between 4 and 8. Chloroquine phosphate and chloroquine sulphate, for example, are sensitive to light, and may be dispensed in opaque bottles.

Example 1

A 4-aminoquinoline compound, such as Chloroquine phosphate equivalent to chloroquine 30 mg. Sodium chloride 0.9 gins, Benzalkonium chloride 5 mg, are mixed to dissolve in purified sterile water. Purified sterile water is then added to produce a total volume of 100 mL.

Example 2

A 4-aminoquinoline compound, such as Chloroquine phosphate equivalent to chloroquine 100 mg, Sodium chloride 0.9 gms, Benzalkonium chloride 5 mg, are mixed to dissolve in purified sterile water. Purified sterile water is then added to produce a total volume of 100 mL.

Example 3

A 4-aminoquinoline compound, such as Chloroquine phosphate equivalent to chloroquine 1 mg, Sodium chloride 0.9 gms, Benzalkonium chloride 5 mg are mixed to dissolve in purified sterile water. Purified sterile water is then added to produce a total volume of 100 mL.

Example 4

Ophthalmic Ointment

A 4-aminoquinoline compound such as Chloroquine phosphate is admixed with mineral oil and white petrolatum to form an ointment containing 0.05 weight percent active 4-aminoquinoline compound.

It will be appreciated that any of the 4-aminoquinoline compounds described herein could be employed in any of these representative formulations taking into account solubility, dispersability and the like, and that any of these formulations could be administered in any of the above described manners so as to treat ocular inflammation.

Method of Drug Delivery

Any of the 4-aminoquinoline compounds (including salts thereof) employed in this invention may be formulated into ophthalmic pharmaceutical compositions suitable for topical administration.

The active ingredients can be administered in the conjunctival sack as eye drops, ointments, gels, sustained release carriers, slow dissolving capsules placed in the conjunctival sack, via release from a contact lens, subconjunctivally by injection, or intravitreally by injection, by preparing a suitable formulation of the active ingredient and utilizing procedures well known to those skilled in the art. Preferably, the formulations are prepared with suitable non-toxic pharmaceutically acceptable ingredients. These ingredients are known to those skilled in the preparation of eyedrops, eyeointments, subconjunctival and intravitreal injections. Some of these ingredients can be found in Remington's Pharmaceutical Sciences, 17th edition, 1985, a standard reference in the field. The choice of suitable carriers is highly dependent upon the exact nature of the eyedrops, eyeointments, subconjunctival, intravitreal dosage form desired, e.g. solutions, sprays, drops, gels, pastes, patches.

The 4-aminoquinoline derivatives may be administered via a biocompatible and implantable controlled-release drug delivery device as taught in U.S. Pat. No. 6,331,313, to Wong. The 4-aminoquinoline compounds employed in this invention can also be administered in sustained release forms or from sustained release drug delivery systems which can be found in Remington's Pharmaceutical Sciences, 17th edition, 1985, Mack Publishing Company, Easton, Pa., and International Programme on Chemical Safety (IPCS).

In one of the more preferred embodiments, the ophthalmic carrier is a conjunctival insert. Preparation of said inserts is taught by U.S. Pat. No. 6,217,896 to Benjamin and other methods are well known in the art.

Method of Treating Ocular Inflammation

One object of the invention is to provide a method for treating ocular inflammation comprising topically applying to the eye an ophthalmic pharmaceutical composition comprising a pharmaceutically acceptable ophthalmic carrier and an ocular inflammation-treating amount of one or more 4-aminoquinoline compounds, or one of their pharmaceutically acceptable analogues or salts.

The inventor has discovered unexpectedly that by administering a 4-aminoquinoline compound topically directly into the eye, the much feared ocular toxicity is avoided rather than enhanced.

Any of the formulations and methods of drug delivery disclosed in this invention may be used to treat ocular inflammation by direct application of a 4-aminoquinoline compound to the eye.

The conditions treated with the ophthalmic pharmaceutical compositions of this invention generally include ocular inflammation and the various symptoms which fall within the ocular inflammation definition. These include, for example, uveitis. The 4-aminoquinoline formulations provided by this invention can be administered to achieve an inflammation reducing effect in the eye. To achieve this effect, a topical preparation is administered directly to the inflamed eye by instilling adequate topical solution or salve or ointment to the inflamed eye to reduce the inflammation. Typically, the concentration will range from about 0.001 nanograms per milliliter and 10.00 milligrams and the dose will range from two to twelve drops per day, administered at intervals throughout the day.

Ophthalmic pharmaceutical compositions comprising a pharmaceutically acceptable ophthalmic carrier and an ocular inflammation-treating amount of one or more 4-aminoquinoline compounds are effective in preventing and treating ocular inflammation of any etiology. Said opthalmic pharmaceutical compositions are also effective in treating retinitis pigmentosa.

Non-limiting examples include 1) Ocular inflammation related to allergy, infection, pain in the eye, non-infectious inflammation triggered by immunological factors, surgery, chemical or mechanical injury, injury due to exposure to radiation, infrared or ultraviolet rays, degenerative changes or dystrophies; 2) Ocular inflammation related urticaria, allergic conjunctivitis, vernal conjunctivitis, inflammation of the eye, allergic responses in the eye, uveitis, iritis, iridocyclitis, scleritis, episcleritis, choroiditis, optic neuritis, Mooren's ulcer, ulcerative keratitis associated with rheumatoid arthritis, anterior uveitis, Thygeson's punctate keratitis, or other immunological reactions; 3) Ocular inflammation related to an infection of the eye by any one or more infective agents such as viruses including adenovirus and cytomegalovirus, fungi including toxoplasmosis, bacteria including tuberculosis and syphilis, chlamydia, and amoeba; 4) Ocular inflammation related to uveitis such as Behect's disease, pars planitis, idiopathic uveitis, ocular sarcoid, sympathetic ophthalmia, idiopathic vitritis, vitritis, or uveitis resulting from trauma; 5) Retinitis pigmentosa.

In any treatment regimen, a health care professional should assess the patient's condition and determine whether or not the patient would benefit from 4-aminoquinoline treatment. Some routine dosage adjustments may be necessary to achieve an optimal dosage level and pattern.

The compounds of this invention can be administered as the sole active agent or they can be administered in combination with other agents, including other active 4-aminoquinoline compounds.

In one preferred embodiment of the invention, said ophthalmic pharmaceutical composition is administered as ophthalmic drops, ophthalmic salve, ophthalmic suspension, opthalmic ointment, ophthalmic spray, subconjunctival injection, or intravitreal injection or via a contact lens, ocular time release insert, liposomal composition, or sustained release implant. In another embodiment, it is delivered in a conjunctival insert according the U.S. Pat. No. 6,217,896 to Benjamin.

In one of its method aspects, this invention is directed to a method for treating a mammal with ocular inflammation which method comprises administering to said mammal a pharmaceutical composition comprising a pharmaceutically acceptable ophthalmic carrier and an ocular inflammation-treating amount of a 4-aminoquinoline compound of formula I as described above, and in U.S. Pat. No. 4,421,920 to Baudouin, U.S. Pat. No. 5,596,002, to Hofheinz, and U.S. Pat. No. 5,948,791, to Hofheinz.

In another of its method aspects, this invention is directed to a method for treating a mammal with inflammation which method comprises administering to said mammal a pharmaceutical composition comprising a pharmaceutically acceptable ophthalmic carrier and an inflammation-treating amount of a compound selected from the group consisting of Amodiaquine, Chloroquine, and Hydroxychloroquine, and the derivatives, salts and isomers of Amodiaquine, Chloroquine, and Hydroxychloroquine. In another method, ophthalmic pharmaceutical composition comprising a pharmaceutically acceptable ophthalmic carrier and an ocular inflammation-treating an ocular inflammation-treating amount of cletoquine, quinacrine (mepacrine), pyrimethamine, or mefloquine is topically applied to the eye.

In another preferred embodiment of the invention, said ophthalmic pharmaceutical composition is administered as ophthalmic drops in a dose of one to ten drops to the eye per day at intervals of one (1) to ten (10) times per day, one (1) drop on alternative days or one (1) drop per week.

The concentration of the 4-aminoquinoline compound or a salt or isomer of a 4-aminoquinoline derivative in said ophthalmic pharmaceutical composition is preferably about 0.001 nanograms per milliliter and 10.00 milligrams per milliliter.

Most preferably, the 4-aminoquinoline derivative is selected from the group consisting of Amodiaquine, Chloroquine, and Hydroxychloroquine, and the derivatives, salts and isomers of Amodiaquine, Chloroquine, and Hydroxychloroquine. Cletoquine, mefloquine, quinacrine (mepacrine), or pyrimethamine may also be used.

The invention will be further illustrated by the following non-limiting examples:

From the foregoing description, various modifications and changes in the compositions and methods of this invention will occur to those skilled in the art. All such modifications coming within the scope of the appended claims are intended to be included therein. Those skilled in the art will find it apparent that various modifications and variations can be made to the formulations of this invention. Thus, the present invention is intended to cover such modifications and variations, provided that they come within the scope of the appended claims and their equivalents.

The disclosures of all publications cited above are expressly incorporated by reference in their entireties to the same extent as if each were incorporated by reference individually.

The invention claimed is:

1. An ophthalmic pharmaceutical composition comprising a pharmaceutically acceptable ophthalmic carrier and about 0.001 nanograms per milliliter to 1.0 milligrams per milliliter of a 4-aminoquinoline compound of formula I:

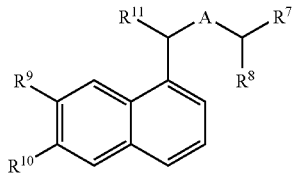

wherein A is

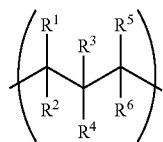

, $(C(R^3)(R^4))_n$;
or
A is

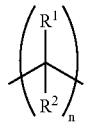

or $(C_5\ C_6)$-cycloalkylene; n is 1–4;
or
A is an alkyl of 1 through 5 carbon atoms substituted by a dialkylamino group of which each alkyl radical contains 1 through 4 carbon atoms, phenyl, or phenyl substituted by one or more radicals selected from carboxy and hydroxy and alkyl radicals of 1 through 4 carbon atoms and $R^9$ is hydrogen or halogen; and $R^{10}$ is halogen or trifluoromethyl;

and $R^1$ to $R^6$ are hydrogen or in which one or two of $R^1$ to $R^6$ are independently selected from alkyl and the other substituents are hydrogen; $R^7$ and $R^8$ are independently selected from alkyl, alkenyl or aralkyl, or together with the N atom signify pyrrolidine or piperidine, either or both of which may be substituted by alkyl; and n=0 or 1; or wherein $R^1$ and $R^3$ are tri- or tetramethylene; $R^2$ and $R^4$ to $R^6$ are hydrogen; n=0; and $R^7$ and $R^8$ are defined as above; or wherein $R^1$ and $R^7$ are methylene or dimethylene and n=1, or $R^3$ and $R^7$ are di- or trimethylene and n=0, or $R^3$ and $R^7$ are di- or trimethylene and n=1, or $R^3$ and $R^7$ are tri- or tetramethylene and n=0, or $R^5$ and $R^7$ are tri- or tetramethylene and n=1, or $R^1$ and $R^5$ are di- or tri-methylene and n=1, and the remaining substituents are hydrogen, except $R^8$ which is selected from alkyl, alkenyl or alkynyl; or wherein $R^3$ and $R^5$ are tri- or tetramethylene and n=1; $R^1$, $R^2$, $R^4$ and $R^6$ are hydrogen; and $R^7$ and $R^8$ are selected from alkyl, alkenyl or aralkyl or together with the N atom are pyrrolidine or piperidine, either or both of which may be substituted by alkyl;

$R^9$ is hydrogen or halogen; and $R^{10}$ is halogen or trifluoromethyl;

$R^{11}$ is a hydrogen atom or an alkyl radical (1–5 carbon atoms); or $R^7$ is hydrogen and $R^8$ is $(CH_2)_p$-B and p is 1–3;

B is aryl selected from phenyl, phenyl mono-, di-, or tri-substituted by substituent from the group consisting of halogen, hydroxy, lower alkyl, lower alkoxy, trifluoromethyl, cyano, di-lower alkylamino or their N-oxides, phenyloxy, phenyl, and methylsuphanyl, naphthyl, benzo[1,3]dioxol, or monocyclic aromatic heterocycle with 1 or 2 heteroatoms selected from N and O;

and $R^9$ is hydrogen or halogen; and $R^{10}$ is halogen or trifluoromethyl;

as well as pharmaceutically acceptable salts of basic compounds of formula I.

* * * * *